United States Patent [19]

Ito et al.

[11] Patent Number: 5,591,759
[45] Date of Patent: Jan. 7, 1997

[54] AQUEOUS ISOTHIAZOLONE FORMULATION

[75] Inventors: Yosuke Ito, Otsu; Yoichi Sano, Takatsuki; Katsuji Tsuji, Kyoto; Sakae Katayama, Osaka, all of Japan

[73] Assignee: Katayama Chemical, Inc., Osaka, Japan

[21] Appl. No.: 185,272

[22] Filed: Jan. 24, 1994

Related U.S. Application Data

[63] Continuation of Ser. No. 892,679, Jun. 4, 1992, abandoned, which is a continuation of Ser. No. 524,036, May 16, 1990, abandoned.

[30] Foreign Application Priority Data

May 17, 1989 [JP] Japan ..................... 1-125370

[51] Int. Cl.⁶ .................... A01N 31/02; A01N 43/80; C02F 1/76; C08J 3/00
[52] U.S. Cl. .................... 514/372; 514/724; 514/727; 514/970; 422/28; 422/37; 162/161; 106/18.32; 106/18.33; 210/749; 210/755; 523/122
[58] Field of Search ................... 514/372, 724, 514/727, 970; 422/28, 37; 162/161; 106/18.32, 18.33; 210/749, 755; 523/122

[56] References Cited

U.S. PATENT DOCUMENTS

| | | | |
|---|---|---|---|
| 3,558,788 | 1/1971 | Clark et al. | 514/727 |
| 3,879,559 | 4/1975 | Shema et al. | 514/372 |
| 3,929,562 | 12/1975 | Shema et al. | 514/372 |
| 4,265,899 | 5/1981 | Lewis et al. | 514/372 |
| 4,723,044 | 2/1988 | Wantanabe et al. | 568/713 |
| 4,732,905 | 3/1988 | Donofrio et al. | 514/372 |
| 4,822,511 | 4/1989 | Law | 514/372 |
| 4,906,651 | 3/1990 | Hsu | 514/372 |
| 5,306,725 | 4/1994 | Sano et al. | 514/372 |

FOREIGN PATENT DOCUMENTS

| | | |
|---|---|---|
| 0166611 | 1/1986 | European Pat. Off. |
| 0196452 | 10/1986 | European Pat. Off. |
| 60-96652 | 4/1985 | Japan |
| 60-65042 | 5/1985 | Japan |
| 60-54281 | 11/1985 | Japan |
| 63-316702 | 12/1988 | Japan |

*Primary Examiner*—John Pak
*Attorney, Agent, or Firm*—Merchant, Gould, Smith, Edell, Welter & Schmidt, P.A.

[57] ABSTRACT

An aqueous isothiazolone formulation useful for antiseptic or antifungal treatment of various synthetic polymeric emulsions, which comprises (a) a specific isothiazolone compound, (b) water or an aqueous solvent and (c) a specific nitrobromo or cyanobromo compound.

5 Claims, No Drawings

AQUEOUS ISOTHIAZOLONE FORMULATION

This application is a continuation of U.S. application Ser. No. 07/892,679 filed Jun. 4, 1992, now abandoned; which is a continuation of U.S. application Ser. No. 07/524,036 filed May 16, 1990, now abandoned.

BACKGROUND OF THE INVENTION

1. Field of the Invention

The present invention concerns a stabilized aqueous isothiazolone formulation. More in particular, it relates to an aqueous formulation containing an isothiazolin-3-one compound which is useful as non-medicinal biocide and, in particular, useful for antiseptic or antifungal treatment of various emulsions of synthetic polymer.

2. Description of the Prior Art

Isothiazolone compounds such as 5-chloro-2-methyl-isothiazolin-3-one and 2-methyl-isothiazolin-3-one have been known so far as non-medicinal biocide, antiseptic or antifungal agent which are useful, in particular, as antiseptic or antifungal agent for emulsions of synthetic polymer such as NBR latex, SBR latex or acrylic resin emulsion.

Since the isothiazolone compounds are easily water soluble, it is desirable to use them in the form of an aqueous solution in view of dispersion into systems to be treated, flammability of products and also from an economical point of view. Referring to the flammability, those products formulated only with a glycol solvent exhibit a flammability.

Sufficient care has to be taken for flammable products so as to prevent the occurrence of fire accident or spread thereof. Therefore, flammable products are hard to be dealt with, especially in storage or transportation.

Accordingly, flashing products are difficult to handle and non-flammable products are desired also for biocides. However, since isothiazolone compounds are hydrolyzed in water in a short period of time, a mere aqueous solution thereof is extremely instable as formulations and can not be put to practical use at all.

In view of the above, an aqueous formulation has been prepared by forming an isothiazolone compound as a complex with a metal salt such as calcium salt or magnesium salt and then dissolving the complex in water or an aqueous solvent for providing stability or an organic solvent formulation has been prepared by dissolving an isothiazolone compound in a great amount of organic solvent with a small amount of water thereby remarkably reducing the water content (Japanese Patent Laid-Open Sho 61-56174 and 61-212576).

However, if the conventional aqueous formulation as described above is added as it is by an effective amount as an antiseptic or antifungal agent to emulsions of synthetic polymer, there is a problem that the emulsion phase is broken to cause phase separation or coagulation (so-called emulsion shock) due to the effect of polyvalent metal ions such as of calcium or magnesium contained in the formulation.

Accordingly, it is necessary upon using such an aqueous solution to sufficiently dilute the same, but this may cause a disadvantage of lowering the quality such as variation off the latex concentration in the emulsions of synthetic polymer as an object for the treatment. Further, coagulation may some time occur even if the additive is used after dilution. In addition, there has been also proposed a use off such an aqueous formulation with no dilution with emulsions of synthetic polymer, but it is necessary to use a special anionic surface active agent in combination (Japanese Patent Laid-Open Sho 60-650421 and Sho 60-96652).

Further, if the organic solvent Formulation as described above is added to emulsions of synthetic polymer, the organic solvent introduced locally at a high concentration in the system tends to cause a shock depending on the case.

The present invention has been made in view of the foregoing situations and it is an object thereof to provide an isothiazolone compound formulation which is excellent in the stability of the formulation, free from the problem of flammability and inexpensive from an economical point of view, as well as causes no shock when added directly to emulsions of synthetic polymer.

Although there has been a suggestion of combining a compound of the ingredient (a) and a compound of a ingredient (c) used in the present invention in a non-aqueous formulation (Japanese Patent Publication Sho 60-54281 and Japanese Patent Laid-Open Sho 63-316702), combination of them in an aqueous formulation and the effect obtained therefrom have not yet been known at all.

SUMMARY OF THE INVENTION

In view of the above, the present inventors have made an earnest study and, as a result, have found that an instable aqueous solution of an isothiazolone compound is remarkably improved in stability without using a metal salt by preparing the formulation with addition of an extremely small amount of a specific bromine compound, and that addition to such an aqueous formulation of an effective antibacterial or antifungal amount to a polymeric emulsion does not result in undesired effects such as shocks.

Thus, according to the present invention, there is provided an aqueous isothiazolone formulation comprising (a) an isothiazolone compound represented by the general formula (I):

(where X represents a hydrogen atom or halogen atom and Y represents an alkyl group), (b) a water or a mixture of water and a hydrophilic organic solvent in an amount at least sufficient to dissolve the compound of the general formula (I) described above, and (c) a nitrobromo or cyanobromo compound blended as a stabilizing ingredient and represented by the following formula (II):

where $X_1$ represents a nitro group or cyano group, $Y_1$, $Y_2$ represents, independently, bromine atom, nitro group, cyano group, aminocarbonyl group, a lower alkyl group substituted with a bromine atom, cyano group or hydroxy group, or

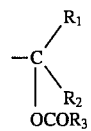

($R_1$, $R_2$ and $R_3$ represent, independently, a lower alkyl group or hydrogen atom), or either one of $Y_1$ or $Y_2$ represents

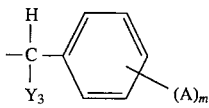

while the other of them represents hydrogen or bromine atom or $Y_1$ and $Y_2$ are joined together to form

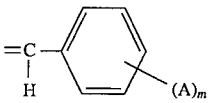

in which $Y_3$ represents a hydrogen atom or halogen atom, A represents a hydrogen atom, halogen atom, nitro group or lower alkyl group and m represents an integer of 1 to 3, or $Y_1$ and $Y_2$ are joined together to form a dioxane group which may be substituted with a lower alkyl group.

DESCRIPTION OF THE PREFERRED EMBODIMENTS

The aqueous formulation according to the present invention is a solution applied with excellent formulation stability substantially free from calcium or magnesium salt which has been used for the stabilization. In particular, it has been accomplished on the basis of an unexpected finding that the bromine compound functions as a stabilizer.

It has been known that certain bromine compounds are used in combination with the isothiazolone compound with an aim of synergistic sterilizing effect (Japanese Patent Publication Sho 60-54281). However, this publication actually discloses only a non-aqueous formulation using them together and, in particular, the publication neither shows nor suggests at all that the stabilization of the aqueous formulation of the isothiazolone compound can be attained by the incorporation of a small amount of the bromine compound.

As the halogen atom for the substituent X in the isothiazolone compound off the formula (I) used in the present invention, there can be mentioned, for example, chlorine atom, bromine atom and iodine atom, chlorine atom being preferred. On the other hand, as the lower alkyl group for the substituent Y, there can be mentioned alkyl groups with 1 to 8 carbon atoms (for example, methyl, ethyl, butyl or octyl), methyl group being preferred.

Preferred typical examples of the isothiazolone compounds of the formula (I) are 2-methyl-5-chloro-1,2-isothiazolin-3-one and 2-methyl-1,2-isothiazolin-3-one.

The isothiazolone compounds can be prepared, for example, in accordance with the synthesis method as described in Japanese Patent Publication Sho 46-12723 and they are usually obtained as a mixture of these compounds as above. Such a mixture can also be used suitably in this invention.

In the present invention, the compound of the formula (II) is used as a stabilizer for the formulation. Referring to the lower alkyl group in the definition for the compound (II), alkyl groups with 1 to 8 carbon atoms described above can also be mentioned.

As the specific examples of the compound of the formula (II) described above there can be mentioned, for example, tribromonitromethane, 2,2-dibromo-3-nitrilopropionamide,
2,2-dibromo-2-nitroethanol,
1,1-dibromo-1-nitro-2-propanol,
1,1-dibromo-1-nitro-2-acetoxyethane,
1,1-dibromo-1-nitro-2-acetoxypropane,
2-bromo-2-nitro-1,3-diacetoxypropane,
2-bromo-2-nitro-1,3-diformyloxypropane,
2-nitro-2-bromo-1,3-propanediol.
1,2-dibromo-2,4-dicyanobutane,
2,3-dibromopropionnitrile,
(1,2-dibromo-2-nitroethyl)benzene,
β-bromo-β-nitrostyrene,
(1,2-dibromo-2-nitroethyl)-4-chlorobenzene,
β-bromo-4-chloro-β-nitrostyrene,
β-bromo-β,p-dinitrostyrene,
β-bromo-4-methyl-β-nitrostyrene,
5-bromo-5-nitro-1,3-dioxane, and
5-bromo-2-methyl-5-nitro-1,3-dioxane.

They may be used either alone or as a combination of two or more of them. Among them, 2-nitro-2-bromo-1,3-propanediol,
2-bromo-2-nitro-1,3-diacetoxypropane,
2-bromo-2-nitro-1,3-diformyloxypropane,
2,2-dibromo-2-nitroethanol,
1,1-dibromo-1-nitro-2-propanol,
2,2-dibromo-3-nitrilopropionamide,
tribromonitromethane,
1,2-dibromo-2,4-dicyanobutane,
β-bromo-β-nitrostyrene,
5-bromo-5-nitro-1,3-dioxane, or
5-bromo-2-methyl-5-nitro-1,3-dioxane are preferably used in view of the effect of providing the stability.

The aqueous formulation according to the present invention can be prepared by preparing an aqueous solution of the compound of the formula (I) and adding a required amount of the stabilizing ingredient into the solution. However, the formulation can be prepared with no particular restrictions to such sequence.

As water used here as a solvent, there may be used usual water, for example, tap water, drinking water, purified water, etc. and industrial service water, may also be used. Instead of water, it is also possible to use an aqueous solvent prepared by mixing water with a hydrophilic organic solvent, for example, various known polyols or polyol ether type liquid compounds such as ethylene glycol, diethylene glycol, polyethylene glycol, propylene glycol, dipropylene glycol, tripropylene glycol, polypropylene glycol, 1,4-butanediol, 1,5-pentanediol, ethylene glycol monomethyl ether, ethylene glycol monoethyl ether, ethylene glycol monobutyl ether, diethylene glycol monomethyl ether, diethylene glycol monoethyl ether and tripropylene glycol monomethyl ether; N,N-dimethylformamide, N,N-diethylformamide, N,N-dimethylacetamide and N-methyl-2-pyrrolidone.

When flammability of the formulation is taken into consideration, water content in the formulation is preferably not less than 5% by weight and, in view of preventing the shock of the synthetic polymeric emulsion, the water content in the formulation is preferably not less than 10% by weight and, particularly preferably, not less than 50% by weight in the formulation.

In the case of using the organic solvent as described above for the aqueous formulation according to the present invention, it is possible to prepare a formulation by adding a predetermined amount of the stabilizing ingredient to the solution of the organic solvent of the formula (I) and dilute the formulation with water upon use. In this case, an economical merit in view of transportation is also obtainable.

As the organic solvent used for the organic solvent formulation, an amide compound such as N,N-dimethylformamide, N,N-diethylformamide, N,N-dimethylacetamide and N-methyl-2-pyrrolidone is used alone or as a mixed solvent of such an amide compound and the glycol solvent described above is used preferably in view of the storage stability of the formulation.

The blending amount of the compound of the formula (I) in the aqueous formulation according to the present invention is preferably from 1 to 30% by weight and, more preferably, 1 to 20% by weight in view or the storage stability.

The blending amount of the nitrobromo or cyanobromo compound as the stabilizing agent is preferably from 0.001 to 0.1 parts by weight and, more preferably, of not less than 0.004 parts by weight based on one part by weight of the compound of the formula (I) in view of the storage stability. However, since the stabilizing effect is usually obtained equally even if it is added by more than 0.1 parts by weight, the compound may be added in a greater amount. If it is less than 0.001 parts by weight, it is not preferred since the isothiazolone compound becomes more hydrolyzable and an aqueous formulation of excellent storage stability can not be obtained. On the other hand, it may be added by more than 0.1 part by weight but it is preferably added up to 0.1 part by weight from an economical point of view.

In the aqueous formulation according to the present invention, since a polyvalent metal is not used and, in addition, an organic solvent is not used or used only at a remarkably reduced amount, shock upon adding to the synthetic polymeric emulsion can be prevented or suppressed. In addition, it is free from inconvenience in handling such as flammability; the formulation is inexpensive and can provide excellent stability as the aqueous formulation.

EXAMPLE 1

Formulations of Examples 1B–56B and Comparative Examples 1A–75A were prepared by using a mixture of 2-methyl-5-chloro-isothiazolin-3-one and 2-methyl-isothiazolin-3-one (at 9:1 weight ratio) (hereinafter simply referred to as MIT) as a isothiazolone compound, dissolving the mixture in each of solvents as described in Table 1, and further admixing a stabilizing ingredient under stirring (all of numerals in the table represent parts by weight).

The following tests were carried out for each of the formulation products.
(Store Stability Test)
Test method—Each of the formulations was placed in a glass vessel and left under the condition of 40° C. The state with elapse of time was observed and the results were expressed as "o" for the formulation showing no decomposition, as "Δ" for the formulation showing slight clouding in appearance and MIT decomposition rate of less than 5% as measured by HPLC and as "x" for the formulation showing clouding in view of the appearance due to great amount of crystals deposited and decomposition rate of not less than 5%.

It is estimated from the test result for long years that stability for 2 months at 40° C. in this test will correspond to the stability at a room temperature for more than 6 months.
(Shock Test to Polymeric Emulsion)

The polymeric emulsion (two kinds of SBR latex and acrylic resin emulsion) was taken in 100 ml and 200 ml volume beakers respectively, to which 3 ml of the formulation was added. After stirring with a magnetic stirrer for 3 min, the content was filtered through 100 mesh metal mesh. The specimens showing no coagulation products on the metal mesh were expressed as "o" and those leaving coagulation products as "x". The results are shown in Table 1.

From the results, it can be seen that the aqueous preparation according to the present invention is excellent in the stability and causes no undesired effect on the polymeric emulsion.

In the table, abbreviations mean the following compounds.

| Abbreviation | Compound Name |
| --- | --- |
| DMF | N,N-dimethylformamide |
| DEF | N,N-diethylformamide |
| DMAA | N,N-dimethylacetamide |
| MP | N-methyl-2-pyrrolidone |
| EG | Ethylene glycol |
| DEG | Diethylene glycol |
| PEG-200 | Polyethylene glycol (average molecular weight 200) |
| PG | Propylene glycol |
| DPG | Dipropylene glycol |
| TPG | Tripropylene glycol |
| MDG | Diethylene glycol monomethyl ether |
| MEG | Ethylene glycol monomethyl ether |
| EDG | Diethylene glycol monoethyl ether |
| TPM | Tripropylene glycol monomethyl ether |
| 1,4-BD | 1,4-butanediol |
| 1,5-PD | 1,5-pentanediol |

| Abbreviation | Structure | Name of Compound |
| --- | --- | --- |
| Bronopole | HO—CH$_2$—C(NO$_2$)(Br)—CH$_2$—OH | 2-nitro-2-bromo-1,3-propanediol |
| MAC | CH$_3$—C(=O)—O—CH$_2$—C(NO$_2$)(Br)—CH$_2$—O—C(=O)—CH$_3$ | 2-bromo-2-nitro-1,3 diacetoxy-propane |
| DBNE | Br—C(NO$_2$)(Br)—CH$_2$—OH | 2,2-dibromo-2-nitroethanol |

-continued

| Abbreviation | Name of Compound | |
|---|---|---|
| DBNP | Br—C(NO$_2$)(Br)—CH$_2$—CH$_3$ with OH | 1,1-dibromo-1-nitro-2-propanol |
| DBNPA | Br—C(Br)(C≡N)—C(=O)—NH$_2$ | 2,2-dibromo-3-nitrilo propionamide |
| TBNM | Br—C(NO$_2$)(Br)—Br | tribromonitro-methane |

TABLE 1

| Formulation No. | Preparation (parts by weight) | | | | | | Storage stability 40° C. (day) | | | | | | Effect on latex | | |
|---|---|---|---|---|---|---|---|---|---|---|---|---|---|---|---|
| | MIT | Glycol solvent | | Amide solvent | | Stabilizing ingredient | | Water | 7 | 14 | 21 | 30 | 45 | 60 | SBR latex pH 7.9 | SBR latex pH 8.6 | Acrylic resin emulsion pH 7.6 |
| 1-A | 6.0 | EG | 93.994 | — | | DBNE | 0.006 | | O | O | O | O | X | X | X | X | X |
| 1-B | " | " | " | — | | " | " | 100 | O | X | | | | | O | O | O |
| 2-A | 6.0 | " | 93.99 | — | | " | 0.01 | | O | O | O | O | Δ | X | X | X | X |
| 2-B | " | " | " | — | | " | " | 100 | O | O | O | Δ | X | | O | O | O |
| 3-A | 6.0 | " | 93.98 | — | | " | 0.02 | | O | O | O | O | Δ | X | X | X | X |
| 3-B | " | " | " | — | | " | " | 100 | O | O | O | O | Δ | X | O | O | O |
| 4-A | 6.0 | " | 93.97 | — | | " | 0.03 | | O | O | O | O | Δ | X | X | X | X |
| 4-B | " | " | " | — | | " | " | 100 | O | O | O | O | O | O | O | O | O |
| 5-A | 6.1 | " | 93.3 | — | | " | 0.6 | | O | O | O | O | Δ | X | X | X | X |
| 5-B | " | " | " | — | | " | " | 100 | O | O | O | O | O | O | O | O | O |
| 6-A | 6 | 1,4-BD | 98.0 | — | | " | 6 | | O | O | O | O | Δ | X | X | X | X |
| 6-B | " | " | " | — | | " | " | 100 | O | O | O | O | O | O | O | O | O |
| 7-A | " | | — | DMF | 93.5 | DBNE | 0.5 | | O | O | O | O | O | O | X | X | X |
| 7-B | " | | — | " | " | " | " | 100 | O | O | O | O | O | O | O | O | O |
| 8-A | 6 | | — | DEF | 93.5 | " | 0.5 | | O | O | O | O | O | O | X | X | X |
| 8-B | " | | — | " | " | " | " | 100 | O | O | O | O | O | O | O | O | O |
| 9-A | 6 | | — | DMAA | 93.5 | " | 0.5 | | O | O | O | O | O | O | X | X | X |
| 9-B | " | | — | " | " | " | " | 100 | O | O | O | O | O | O | O | O | O |
| 10-A | 6 | | — | MP | 93.5 | " | 0.5 | | O | O | O | O | O | O | X | X | X |
| 10-B | " | | — | " | " | " | " | 100 | O | O | O | O | O | O | O | O | O |
| 11-A | 5 | 1,4BD | 94.994 | — | | MAC | 0.005 | | O | O | O | O | X | X | X | X | X |
| 11-B | " | " | " | — | | " | " | 100 | O | O | X | | | | O | O | O |
| 12-A | 5 | " | 94.99 | — | | " | 0.01 | | O | O | O | O | Δ | X | X | X | X |
| 12-B | " | " | " | — | | " | " | 100 | O | O | O | O | Δ | X | O | O | O |
| 13-A | 5 | " | 94.98 | — | | " | 0.02 | | O | O | O | O | Δ | X | X | X | X |
| 13-B | " | " | " | — | | " | " | 100 | O | O | O | O | O | Δ | O | O | O |
| 14-A | 5 | " | 94.97 | — | | " | 0.03 | | O | O | O | O | Δ | X | X | X | X |
| 14-B | " | " | " | — | | " | " | 100 | O | O | O | O | O | O | O | O | O |
| 15-A | 3 | " | 97 | — | | " | 3 | | O | O | O | O | Δ | X | X | X | X |
| 15-B | " | " | " | — | | " | " | 100 | O | O | O | O | O | O | O | O | O |
| 16-A | 5 | | — | DMF | 94.5 | MAC | 0.5 | | O | O | O | O | O | O | X | X | X |
| 16-B | " | | — | " | " | " | " | 100 | O | O | O | O | O | O | O | O | O |
| 17-A | 5 | | — | DMF | 94.5 | " | 0.5 | | O | O | O | O | O | O | X | X | X |
| 17-B | " | | — | " | " | " | " | 100 | O | O | O | O | O | O | O | O | O |
| 18-A | 5 | | — | DMAA | 94.5 | " | 0.5 | | O | O | O | O | O | O | X | X | X |
| 18-B | " | | — | " | " | " | " | 100 | O | O | O | O | O | O | O | O | O |
| 19-A | 5 | | — | MP | " | " | 0.5 | | O | O | O | O | O | O | X | X | X |
| 19-B | " | | — | " | " | " | " | 100 | O | O | O | O | O | O | O | O | O |
| 20-A | 5 | EG | 94.5 | — | | MAC | 0.5 | | O | O | O | O | X | X | X | X | X |
| 20-B | " | " | " | — | | " | " | 100 | O | O | O | O | O | O | O | O | O |
| 21-A | 5 | DEG | " | — | | " | 0.5 | | O | O | O | O | X | X | X | X | X |
| 21-B | " | " | " | — | | " | " | 100 | O | O | O | O | O | O | O | O | O |
| 22-A | 5 | PEG | " | — | | " | 0.5 | | O | O | O | O | X | X | X | X | X |
| 22-B | " | " | " | — | | " | " | 100 | O | O | O | O | O | O | O | O | O |
| 23-A | 5 | PG | " | — | | " | 0.5 | | O | O | O | O | X | X | X | X | X |
| 23-B | " | " | " | — | | " | " | 100 | O | O | O | O | O | O | O | O | O |
| 24-A | 5 | DPG | " | — | | " | 0.5 | | O | O | O | O | X | X | X | X | X |
| 24-B | " | " | " | — | | " | " | 100 | O | O | O | O | O | O | O | O | O |

TABLE 1-continued

| Formulation No. | MIT | Glycol solvent | | Amide solvent | | Stabilizing ingredient | | Water | Storage stability 40° C. (day) | | | | | | SBR latex pH 7.9 | SBR latex pH 8.6 | Acrylic resin emulsion pH 7.6 |
|---|---|---|---|---|---|---|---|---|---|---|---|---|---|---|---|---|---|
| | | | | | | | | | 7 | 14 | 21 | 30 | 45 | 60 | | | |
| 25-A | 5 | TPG | " | — | | " | 0.5 | | O | O | O | O | X | X | X | X | X |
| 25-B | " | " | " | — | | " | " | 100 | O | O | O | O | O | O | O | O | O |
| 26-A | 5 | 1,5-PD | " | — | | " | 0.5 | | O | O | O | O | X | X | X | X | X |
| 26-B | " | " | " | — | | " | " | 100 | O | O | O | O | O | O | O | O | O |
| 27-A | 5 | MDG | " | — | | " | 0.5 | | O | O | O | Δ | X | X | X | X | X |
| 27-B | " | " | " | — | | " | " | 100 | O | O | O | O | O | O | O | O | O |
| 28-A | 5 | MEG | " | — | | " | 0.5 | | O | O | O | Δ | X | X | X | X | X |
| 28-B | " | " | " | — | | " | " | 100 | O | O | O | O | O | O | O | O | O |
| 29-A | 5 | EDG | " | — | | " | 0.5 | | O | O | O | O | X | X | X | X | X |
| 29-B | " | " | " | — | | " | " | 100 | O | O | O | O | O | O | O | O | O |
| 30-A | 5 | TPM | " | — | | " | 0.5 | | O | O | O | O | X | X | X | X | X |
| 30-B | " | " | " | — | | " | " | 100 | O | O | O | O | O | O | O | O | O |
| 31-A | 5.5 | DEG | 94 | — | | DBNE | 0.5 | | O | O | O | O | X | | X | X | X |
| 31-B | " | " | " | — | | " | " | 100 | O | O | O | O | O | O | O | O | O |
| 32-A | 5.5 | DPG | 94 | — | | " | 0.5 | | O | O | O | O | X | | X | X | X |
| 32-B | " | " | " | — | | " | " | 100 | O | O | O | O | O | O | O | O | O |
| 33-A | 5.5 | 1,4-BD | 94 | — | | " | 0.5 | | O | O | O | O | X | | X | X | X |
| 33-B | " | " | " | — | | " | " | 100 | O | O | O | O | O | O | O | O | O |
| 34-A | 5.5 | EG | 94 | — | | Bronopole | 0.5 | | O | O | O | O | X | | X | X | X |
| 34-B | " | " | " | — | | " | " | 100 | O | O | O | O | O | O | O | O | O |
| 35-A | 5.5 | DEG | 94 | — | | " | 0.5 | | O | O | O | O | X | | X | X | X |
| 35-B | " | " | " | — | | " | " | 100 | O | O | O | O | O | O | O | O | O |
| 36-A | 5.5 | DPG | 94 | — | | " | 0.5 | | O | O | O | O | X | | X | X | X |
| 36-B | " | " | " | — | | " | " | 100 | O | O | O | O | O | O | O | O | O |
| 37-A | 5.5 | 1,4-BD | 94 | — | | " | 0.5 | | O | O | O | O | X | | X | X | X |
| 37-B | " | " | " | — | | " | " | 100 | O | O | O | O | O | O | O | O | O |
| 38-A | 5 | EG | 94.5 | — | | DBNPA | 0.5 | | O | O | O | O | X | | X | X | X |
| 38-B | " | " | " | — | | " | " | 100 | O | O | O | O | O | O | O | O | O |
| 39-A | 5 | DEG | 94.5 | — | | " | 0.5 | | O | O | O | O | X | | X | X | X |
| 39-B | " | " | " | — | | " | " | 100 | O | O | O | O | O | O | O | O | O |
| 40-A | 5 | DPG | 94.5 | — | | " | 0.5 | | O | O | O | O | X | | X | X | X |
| 40-B | " | " | " | — | | " | " | 100 | O | O | O | O | O | O | O | O | O |
| 41-A | 5 | 1,4-BD | 94.5 | — | | " | 0.5 | | O | O | O | O | X | O | X | X | X |
| 41-B | " | " | " | — | | " | " | 100 | O | O | O | O | O | O | O | O | O |
| 42-A | 5 | EG | 94.5 | — | | DBNP | 0.5 | | O | O | O | O | Δ | X | X | X | X |
| 42-B | 5 | " | " | — | | " | " | 100 | O | O | O | O | O | O | O | O | O |
| 43-A | 5 | 1,4-BD | 94.5 | — | | " | 0.5 | | O | O | O | O | Δ | X | X | X | X |
| 43-B | 5 | " | " | — | | " | " | 100 | O | O | O | O | O | O | O | O | O |
| 44-A | 5 | EG | 94.5 | — | | TBNM | 0.5 | | O | O | O | O | Δ | X | X | X | X |
| 44-B | 5 | " | " | — | | " | " | 100 | O | O | O | O | O | O | O | O | O |
| 45-A | 5 | 1,4-BD | 94.5 | — | | " | 0.5 | | O | O | O | O | Δ | X | X | X | X |
| 45-B | 5 | " | " | — | | " | " | 100 | O | O | O | O | O | O | O | O | O |
| 46-A | 5 | EG | 94.98 | — | | MAC | 0.02 | | O | O | O | O | Δ | X | X | X | X |
| 46-B | 5 | " | " | — | | " | " | 100 | O | O | O | O | O | O | O | O | O |
| 47-A | 5 | EG | 89.98 | DMF | 5 | " | 0.02 | | O | O | O | O | O | O | X | X | X |
| 47-B | 5 | " | " | " | " | " | " | 100 | O | O | O | O | O | O | O | O | O |
| 48-A | 5 | — | | DMF | 94.98 | " | 0.02 | | O | O | O | O | O | O | X | X | X |
| 48-B | 5 | — | | " | " | " | " | 100 | O | O | O | O | Δ | X | O | O | O |
| 49-A | 5 | EG | 94.98 | — | | DBNE | 0.02 | | O | O | O | O | Δ | X | X | X | X |
| 49-B | 5 | " | " | — | | " | " | 100 | O | O | O | O | O | O | O | O | O |
| 50-A | 5 | " | 89.98 | DMF | 5 | " | 0.02 | | O | O | O | O | O | O | X | X | X |
| 50-B | 5 | " | " | " | " | " | " | 100 | O | O | O | O | O | O | O | O | O |
| 51-A | 5 | — | | DMF | 94.98 | " | 0.02 | | O | O | O | O | O | O | X | X | X |
| 51-B | 5 | — | | " | " | " | " | 100 | O | O | O | O | Δ | X | O | O | O |
| 55A | 2.5 | EG | 47.5 | | | — | — | 50 | X | | | | | | O | O | O |
| 56A | " | DEG | " | | | — | — | " | X | | | | | | O | O | O |
| 57A | " | PEG200 | " | | | — | — | " | X | | | | | | O | O | O |
| 58A | " | PG | " | | | — | — | " | X | | | | | | O | O | O |
| 59A | " | DPG | " | | | — | — | " | X | | | | | | O | O | O |
| 60A | " | TPG | " | | | — | — | " | X | | | | | | O | O | O |
| 61A | " | 1,4-BD | " | | | — | — | " | X | | | | | | O | O | O |
| 62A | " | 1,5-PD | " | | | — | — | " | X | | | | | | O | O | O |
| 63A | " | MDG | " | | | — | — | " | X | | | | | | O | O | O |
| 64A | " | EDG | " | | | — | — | " | X | | | | | | O | O | O |
| 65A | " | EDG | " | | | — | — | " | X | | | | | | O | O | O |
| 66A | " | TPG | " | | | — | — | " | X | | | | | | O | O | O |
| 67A | " | — | | DMF | 47.5 | — | — | " | X | | | | | | O | O | O |
| 68A | " | | | DEF | " | — | — | " | X | | | | | | O | O | O |
| 69A | " | | | DMAA | " | — | — | " | X | | | | | | O | O | O |
| 70A | " | — | | MP | " | — | — | " | X | | | | | | O | O | O |

TABLE 1-continued

| Formulation No. | MIT | Glycol solvent | | Amide solvent | | Stabilizing ingredient | | Water | Storage stability 40° C. (day) | | | | | | Effect on latex SBR latex pH 7.9 | SBR latex pH 8.6 | Acrylic resin emulsion pH 7.6 |
|---|---|---|---|---|---|---|---|---|---|---|---|---|---|---|---|---|---|
| | | | | | | | | | 7 | 14 | 21 | 30 | 45 | 60 | | | |
| 71A | 5 | EG | 47.5 | — | | — | | — | O | O | O | O | X | | X | X | X |
| 72A | " | DEG | " | — | | — | | — | O | O | O | O | X | | X | X | X |
| 73A | " | DPG | " | — | | — | | — | O | O | O | O | X | | X | X | X |
| 74A | " | 1,4-BD | " | — | | — | | — | O | O | O | O | X | | X | X | X |
| 75A | " | MDG | " | — | | — | | — | O | O | O | X | | | X | X | X |
| 52A | 1 | EG | 98.5 | — | | MAC | 0.5 | — | O | O | O | O | Δ | X | X | X | X |
| 52-B | " | " | " | — | | " | " | 100 | O | O | O | O | O | O | O | O | O |
| 53-A | 10 | EG | 89.5 | — | | MAC | 0.5 | — | O | O | O | O | Δ | X | X | X | X |
| 53-B | " | " | " | — | | " | " | 100 | O | O | O | O | O | O | O | O | O |
| 54-A | 30 | EG | 49.5 | DMF | 20 | MAC | 0.5 | — | O | O | O | O | O | O | X | X | X |
| 54-B | " | " | " | " | " | " | " | 100 | O | O | O | O | O | O | O | O | O |
| 55-B | 5 | — | | — | | DBNE | 0.5 | 94.5 | O | O | O | O | O | O | O | O | O |
| 56-B | 5 | — | | — | | MAC | 0.5 | 94.5 | O | O | O | O | O | O | O | O | O |

EXAMPLE 2

Compounds as shown in the following table were used as the stabilizer and the same tests as in Example 1 were conducted.

| Abbreviation | Name of Compound | |
|---|---|---|
| BNS | 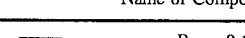 | β-bromo-β-nitrostyrene |
| BND |  | 5-bromo-5-nitro-1,3-dioxane |
| DDB | 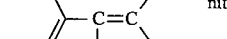 | 1,2-dibromo-2,4-dicyanobutane |

The results are shown in Table 2.

TABLE 2

| Formulation No. | MIT | Glycol solvent | | Amide solvent | | Stabilizing ingredient | | Water | Storage stability 40° C. (day) | | | | | | Effect on latex SBR latex pH 7.9 | SBR latex pH 8.6 | Acrylic resin emulsion pH 7.6 |
|---|---|---|---|---|---|---|---|---|---|---|---|---|---|---|---|---|---|
| | | | | | | | | | 7 | 14 | 21 | 30 | 45 | 60 | | | |
| 76-A | 10 | EG | 89.99 | — | | BND | 0.01 | — | O | O | O | O | X | X | X | X | X |
| 76-B | " | EG | 89.99 | — | | " | 0.01 | 100 | O | O | X | X | X | X | O | O | O |
| 77-A | " | DEG | 89.96 | — | | " | 0.04 | — | O | O | O | O | X | X | X | X | X |
| 77-B | " | " | 89.96 | — | | " | 0.04 | 100 | O | O | O | O | X | X | O | O | O |
| 78-A | " | 1,4-BD | 89.9 | — | | " | 0.1 | — | O | O | O | O | X | X | X | X | X |
| 78-B | " | " | " | — | | " | 0.1 | 100 | O | O | O | O | O | O | O | O | O |
| 79-A | " | PG | 88.0 | — | | " | 2.0 | — | O | O | O | O | X | X | X | X | X |
| 79-B | " | " | " | — | | " | " | 100 | O | O | O | O | O | O | O | O | O |
| 80-A | " | — | | DMAA | 89.9 | " | 0.1 | — | O | O | O | O | O | O | X | X | X |
| 80-B | " | — | | " | " | " | " | 100 | O | O | O | O | O | O | O | O | O |
| 81-A | " | DEG | 84.96 | DMF | 5 | " | 0.04 | — | O | O | O | O | O | O | X | X | X |
| 81-B | " | " | " | " | " | " | " | 100 | O | O | O | O | O | O | O | O | O |
| 82-A | 5.1 | EG | 94.8 | — | | BNS | 0.1 | — | O | O | O | O | X | X | X | X | X |
| 82-B | " | " | " | — | | " | " | 100 | O | O | Δ | X | X | X | O | O | O |
| 83-A | " | MDG | 94.7 | — | | " | 0.2 | — | O | O | O | X | X | X | X | X | X |
| 83-B | " | " | " | — | | " | " | 100 | O | O | O | O | X | X | O | O | O |
| 84-A | " | — | | DMF | 94.4 | " | 0.5 | — | O | O | O | O | X | X | X | X | X |
| 84-B | " | — | | " | " | " | 0.5 | 100 | O | O | O | O | O | O | O | O | O |
| 85-A | " | MDG | 84.7 | DMAA | 10 | " | 0.2 | — | O | O | O | O | O | O | X | X | X |
| 85-B | " | " | " | " | 10 | " | " | 100 | O | O | O | O | O | O | O | O | O |

TABLE 2-continued

| Formulation No. | MIT | Glycol solvent | | Amide solvent | | Stabilizing ingredient | | Water | Storage stability 40° C. (day) | | | | | | SBR latex pH 7.9 | SBR latex pH 8.6 | Acrylic resin emulsion pH 7.6 |
|---|---|---|---|---|---|---|---|---|---|---|---|---|---|---|---|---|---|
| | | | | | | | | | 7 | 14 | 21 | 30 | 45 | 60 | | | |
| 86-A | " | EG | 94.4 | — | | DDB | 0.5 | — | O | O | O | O | X | X | X | X | X |
| 86-B | " | " | " | — | | " | " | 100 | O | O | O | △ | X | X | O | O | O |
| 87-A | " | EG | 89.9 | DMF | 5 | " | " | — | O | O | O | O | O | O | X | X | X |
| 87-B | " | " | " | " | " | " | " | 100 | O | O | O | O | O | O | O | O | O |

EXAMPLE 3

Bronopole, DBNPA, BND, BNS and DDB were used as the stabilizer and the same tests as in Example 1 were conducted. The results are shown in Table 3.

TABLE 3

| Formulation No. | MIT | Glycol solvent | | Amide solvent | Stabilizing ingredient | | Water | Storage stability 40° C. (day) | | | | | | SBR latex pH 7.9 | SBR latex pH 8.6 | Acrylic resin emulsion pH 7.6 |
|---|---|---|---|---|---|---|---|---|---|---|---|---|---|---|---|---|
| | | | | | | | | 7 | 14 | 21 | 30 | 45 | 60 | | | |
| 89-A | 5.5 | EG | 84 | | — | | 10 | X | X | X | X | X | X | O | O | O |
| 89-B | 5.5 | EG | 84.5 | | Bronopole | 0.5 | 10 | O | O | O | O | O | O | O | O | O |
| 90-B | 5.5 | EG | 84 | | DBNPA | 0.5 | 10 | O | O | O | O | O | O | O | O | O |
| 91-B | 5.5 | EG | 84 | | BND | 0.5 | 10 | O | O | O | O | O | O | O | O | O |
| 92-B | 5.5 | EG | 84 | | BNS | 0.5 | 10 | O | O | O | O | O | O | O | O | O |
| 93-B | 5.5 | EG | 84 | | DDB | 0.5 | 10 | O | O | O | O | O | O | O | O | O |

As can be seen from the foregoing examples and comparative examples, the aqueous isothiazolone formulation according to the present invention is excellent in the stability, in particular, storage stability. Then, it causes no undesired effect if added directly to a polymeric emulsion. Accordingly, the formulation is not only convenient upon handling but also enables to extend the regions of application uses and form of uses for the isothiazolone compounds.

What is claimed is:

1. An aqueous isothiazolone formulation consisting essentially of:
   (a) 1–20% by weight of an isothiazolone compound represented by the formula (I):

(I)

where X represents a hydrogen atom or halogen atom and Y represents an alkyl group,
   (b) water or a mixture of water and a hydrophilic organic solvent in an amount at least sufficient to dissolve the compound of the general formula (I) described above, the amount of water in the formulation being at least 5% by weight; and
   (c) a stabilizing-effective amount, in the range of 0.001 to 0.1 part by weight based on one part by weight of the compound of formula (I), of 2,2-dibromo-2-nitroethanol.

2. The formulation of claim 1 in which the isothiazolone compound of the formula (I) is 2-methyl-5-chloro-1,2-isothiazolin-3-one, 2-methyl-1,2-isothiazolin-3-one or mixture thereof.

3. The formulation of claim 1 in which the water content is adjusted to be not less than 10% by weight.

4. The formulation of claim 1 in which component (b) is a mixture of water and a hydrophilic organic solvent.

5. The formulation of claim 4, wherein the hydrophilic organic solvent is selected from the group consisting of ethylene glycol, diethylene glycol, polyethylene glycol, propylene glycol, dipropylene glycol, tripropylene glycol, polypropylene glycol, 1,4-butanediol, 1-5-pentanediol, ethylene glycol monomethyl ether, ethylene glycol monoethyl ether, ethylene glycol monobutyl ether, diethylene glycol monomethyl ether, diethylene glycol monoethyl ether, tripropylene glycol monomethyl ether, N,N-dimethylformamide, N,N-diethylformamide, N,N-dimethylacetamide and N-methyl-2-pyrrolidone.

* * * * *